United States Patent [19]

Livingston et al.

[11] Patent Number: 4,585,006

[45] Date of Patent: Apr. 29, 1986

[54] CARDIAC PACER HAVING STIMULATION THRESHOLD MEASUREMENT CIRCUIT

[75] Inventors: John H. Livingston, Coral Gables; Robert DeCote, Jr., Miami Beach, both of Fla.

[73] Assignee: Cordis Corporation, Miami, Fla.

[21] Appl. No.: 686,620

[22] Filed: Dec. 28, 1984

Related U.S. Application Data

[63] Continuation of Ser. No. 409,328, Aug. 18, 1982, abandoned.

[51] Int. Cl.[4] ............................................. A61N 1/36
[52] U.S. Cl. ......................... 128/419 PG; 128/419 PT
[58] Field of Search ...... 128/419 P, 419 PG, 419 PT, 128/419 R, 421–423

[56] References Cited

U.S. PATENT DOCUMENTS

| | | | |
|---|---|---|---|
| 3,198,195 | 8/1965 | Chardack | 128/419 PG |
| 3,311,111 | 3/1967 | Bowers | 128/419 PT |
| 3,638,656 | 2/1972 | Grandjean et al. | 128/419 PG |
| 3,757,790 | 9/1973 | Herrman | 128/419 PT |
| 3,777,762 | 12/1973 | Nielsen | 128/419 PT |
| 3,800,801 | 4/1974 | Gaillard | 128/419 PT |
| 3,837,348 | 9/1974 | Thaler | 128/419 PT |
| 3,945,387 | 3/1976 | Adams | 128/419 PG |
| 4,024,875 | 5/1979 | Putzke | 128/419 PG |
| 4,030,510 | 6/1977 | Bowers | 128/419 PG |
| 4,387,718 | 6/1983 | Bilitz et al. | 128/419 R |

Primary Examiner—William E. Kamm
Attorney, Agent, or Firm—Lockwood, Alex, FitzGibbon & Cummings

[57] ABSTRACT

An external pacer having a plurality of user-selectable output current levels includes a user-actuable push button switch for reducing the selected output current level by a factor of 10. By observing the absence or presence of an R-wave while operating at the reduced current level the stimulation threshold level of the heart can be determined without the need for additional level selections, and without subjecting the heart to sustained periods of low current. In the illustrated embodiment of the invention for typical output current levels of 2–20 milliamperes threshold levels of 0.2–2.0 milliamperes are obtained.

6 Claims, 3 Drawing Figures

CARDIAC PACER HAVING STIMULATION THRESHOLD MEASUREMENT CIRCUIT

This application is a continuation of application Ser. No. 409,328, filed Aug. 18, 1982, now abandoned.

BACKGROUND OF THE INVENTION

The present invention relates generally to cardiac pacers, and more particularly to improvements in such pacers which provide the capability of determining the stimulation threshold level of a pacer-driven heart with minimal interruption to the normal pacing regimen.

Cardiac pacers, which supply amplitude and rate-controlled electrical pulses to a patient's heart to stimulate muscle contraction, have been developed for both internal applications, wherein the pacer is implanted within the patient's body, and external applications, wherein the pacer is externally carried by the patient and rate, pulse amplitude and sensitivity are adjusted as required by the application. External pacers are typically used in emergency situations, where the patient is waiting implant of a permanent pacer, or where the operation of other pacers is being tested or adjusted. These pacers are connected to the heart by pacer leads which extend into one or more chambers of the heart, and are designed to operate over a wide range of parameters to accommodate physiological changes in the heart and variations in the placement of the pacer leads.

One parameter of particular interest is the minimum current or stimulation threshold required to consistently cause rhythmic contraction of the heart. This stimulation threshold is primarily a function of the size and positioning of the pacer lead tip, and may change from an acute value following initial implant, to a chronic value several weeks or months after the implant, as a result of fibrin growth at the lead-tissue interface. An abnormally high threshold level may indicate that the leads are not making adequate contact with the heart tissue, and that a repositioning of the pacer lead must be accomplished if reliable pacing is to be obtained. Furthermore, knowledge of the threshold level assists the physician in determining the optimum output current level setting for the pacer.

In determining stimulation threshold with prior art external pacers it has been necessary for the operator to readjust the output level controls of the pacers to successively lower settings, observing as the threshold level the output current level at which the heart ceases to rhythmically contract. This has resulted in the normal operating-level stimulation pulse being removed from the heart for undesirably long periods of time while the output level control is repositioned to lower threshold levels through intervening intermediate levels. The present invention is directed to a pacer output circuit which avoids this drawback by enabling the operator to instantaneously switch to a known lower threshold current level from a known higher operating level and back, without having to operate at intermediate levels.

Accordingly, it is a general object of the present invention to provide a new and improved cardiac pacer.

It is a more specific object of the present invention to provide a new and improved cardiac pacer having means for quickly determining the threshold stimulation level of an associated heart.

It is another specific object of the present invention to provide a cardiac pacer having operator-actuated means for instantaneously reducing the current level of stimulation pulses produced by the pacer to enable the threshold level of an associated heart to be determined with minimal interruption to the normal pacing regimen.

SUMMARY OF THE INVENTION

A cardiac pacer for use in conjunction with an external pacer lead for developing recurrent pacing pulses of predetermined current amplitude includes a unidirectional current supply, a capacitor connected in series between the current supply and the pacer lead, and switch means connected between the capacitor and ground and responsive to applied pacer control pulses for applying the charge in the capacitor to the pacer lead. Control circuit means apply control pulses to the switch means as required to produce the pacer pulses. Means including a variable impedance in series with the switch means and the capacitor control the discharge current of the capacitor, and threshold measurement means responsive to a user-initiated control effect increase the variable impedance to reduce the amplitude of the pacing pulse to a predetermined portion of the operating amplitude.

BRIEF DESCRIPTION OF THE DRAWINGS

The features of the present invention which are believed to be novel are set forth with particularity in the appended claims. The invention, together with the further objects and advantages thereof, may best be understood by reference to the following description taken in conjunction with the accompanying drawings, in the several figures of which like reference numerals identify like elements, and in which:

DESCRIPTION OF THE PREFERRED EMBODIMENT

Figure 1:
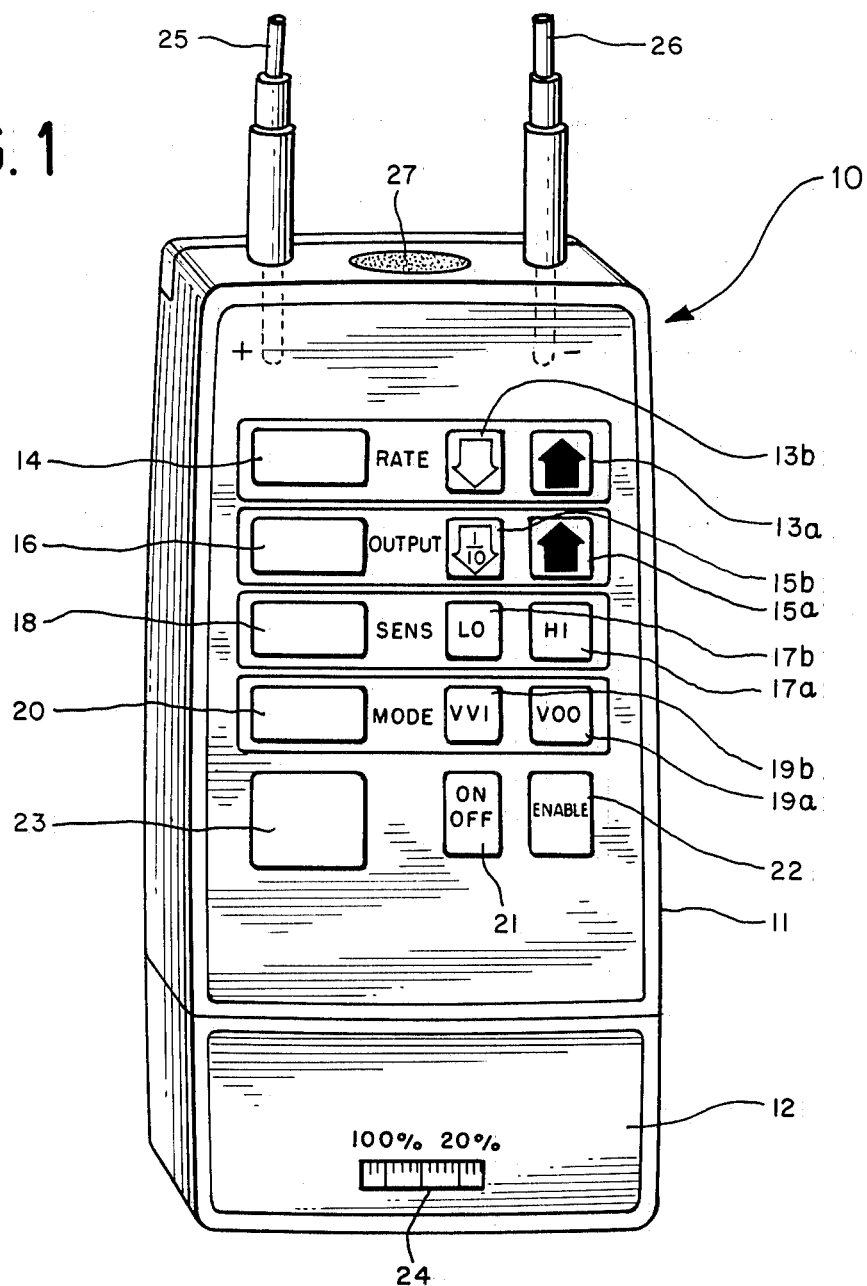
FIG. 1 is a perspective view of an external battery-operated cardiac pacer incorporating a stimulation threshold measurement circuit constructed in accordance with the invention.

Referring to the Figures, and particularly to FIG. 1, the stimulation threshold measurement circuit of the invention may be incorporated in a portable battery-operated cardiac pacer 10 similar to that described in U.S. Pat. No. 4,436,096, issued Mar. 13, 1984. Basically, the pacer includes a generally rectangular housing 11 having a detachable battery pack 12 of complementary dimensions.

The front panel of housing 11 provides various control and indicator functions related to the operation of the pacer. A first pair of increase-decrease push button switches 13a and 13b set output pulse rate. The selected rate, which may typically range from 30 to 150 pulses per minute in steps of five pulses per minute, is displayed by a liquid crystal display (LCD) 14 positioned to one side of the switches. A second pair of increase-decrease push button switches 15a and 15b select output pulse amplitude. The selected amplitude, which may be either 2, 5, 10, 15 or 20 milliamperes, is displayed by means of a second LCD 16. Push button switch 15b has the additional function of activating the stimulation measurement circuit, as will be described presently.

The sensitivity level of the pacer is set by means of a pair of high-low select push button switches 17a and 17b. The low sensitivity level may, for example, correspond to a threshold sensitivity level of approximately 2.5 millivolts, and the high sensitivity level may, for example, correspond to a threshold sensitivity level of approximately 1.0 millivolts. The selected level is indicated by a third LCD 18.

Cardiac pacer 10 is capable of operating in either a ventricular sense and pace demand mode (VVI), or a free running fixed rate ventricular pace mode (VOO). The particular operating mode is selected by the physician by means of a pair of push button switches 19a and 19b, and is indicated by an LCD 20 arranged to the left (as viewed in FIG. 1) of the mode select switches.

The application of power to the pacer is controlled by an ON-OFF push button switch 21. A push button ENABLE switch 22 located to the right of switch 21 must be depressed in order for any of the previously described push buttons, except the pacer ON function of switch 21 and the stimulation threshold measurement function of switch 15b to be operative. Thus, switch 22 serves as an interlock to prevent inadvertent actuation of the other switches and undesired changes to the pacer operating parameters. The fifth LCD 23 located to the left of ON-OFF switch 21 provides an indication of certain specific conditions of the pacer, such as the presence of noise, the occurrence of a low battery condition, the actuation of ENABLE switch 22, the sensing of an R-wave, or the production of an output pulse.

To provide an indication of battery life remaining, the removable battery pack 12 may include on its front panel a battery usage indicator 24. This device, which may for example be a coulometer connected to the battery of the pacer so as to be energized during pacer operation, indicates the cumulative usage of the battery, and hence the estimated battery life remaining.

To provide for electrical connection to the heart of a patient, pacer 10 is provided with a pair of pacer leads 25 and 26 which are physically attached to the heart to sense the occurrence of an R-wave upon ventricular contraction, and to stimulate the muscles of the heart into contraction upon the production of a pacer output pulse. The leads, which may be entirely conventional in design and construction, are received in housing 11 by means of an internal pin connection system whereby once inserted the leads are locked in position and cannot be removed until a single release button 27 on the top of the housing is depressed. This connector system is described and claimed in the co-pending application of George L. Congdon, Ser. No. 210,276, filed Mar. 25, 1980.

Figure 2:
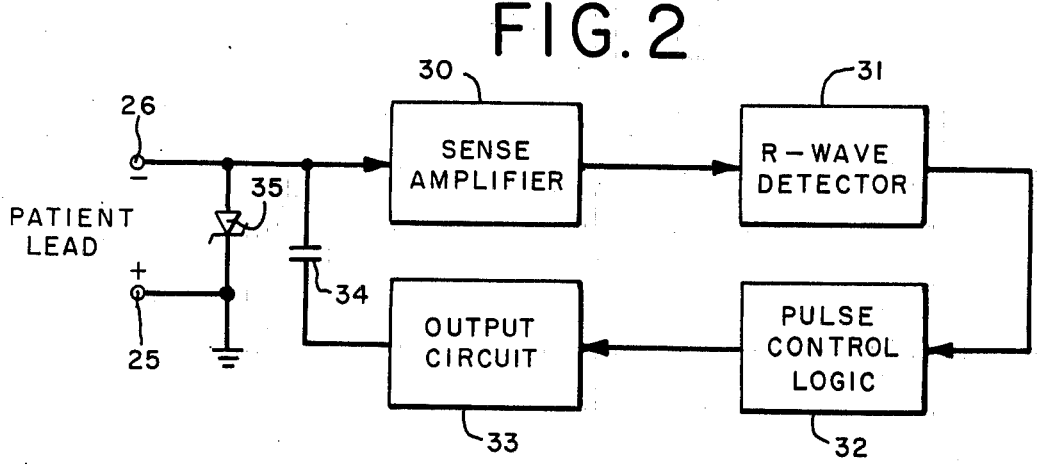
FIG. 2 is a simplified functional block diagram showing the basic operating stages of the pacer.

Referring to FIG. 2, a cardiac pacer 10 in its basic form is seen to include, in accordance with conventional practice, a sense amplifier 30 which amplifies the R-wave conveyed to the pacer by pacer leads 25 and 26. Preferably, amplifier 30 has a bandpass characteristic which attenuates noise and other extraneous signals picked up by pacer leads 25 and 26, so that the detected R-wave may be more effectively amplified for use in the demand mode. The amplified sense signal is applied to an R-wave detector 31, which provides an output pulse upon the occurrence of an R-wave component in the sense signal.

The detector output pulse is applied to a pulse control logic circuit 32, which under appropriate circumstances produces an output control pulse. This control pulse is applied to an output circuit 33 wherein it causes the generation of a pacer output pulse of predetermined amplitude and duration. This pacer output pulse is applied through an output capacitor 34 to pacer leads 25 and 26, which convey the pulse to the heart. An avalanche diode 35, connected between pacer leads 25 and 26, protects the pacer circuitry.

In the demand (VVI) operating mode, pulse control logic circuit 32 causes output circuit 33 to produce a pacer output pulse only in the event that an R-wave resulting from natural heart activity is not detected within a selected time period. In the alternate fixed-rate (VOO) mode, pulse control logic 32 causes the production of pacer output pulses at a rate selected by the user, notwithstanding the presence or absence of R-wave signals at the output of detector 31.

Figure 3:
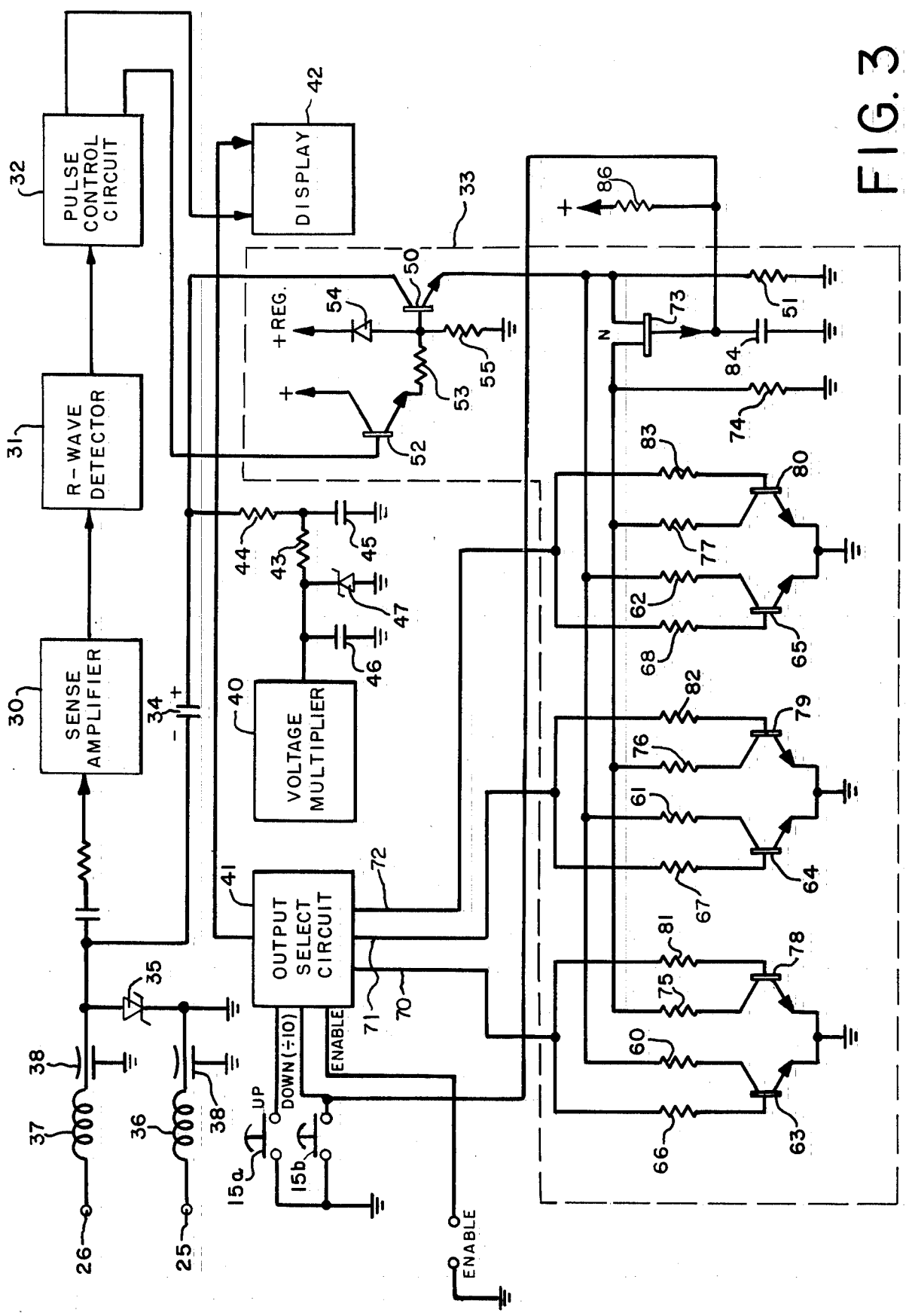
FIG. 3 is a schematic diagram, partially in functional block form, of the pacer showing the pulse output circuit thereof.

Referring to FIG. 3, wherein a more detailed schematic and functional block diagram of the pacer is shown, it is seen that pacer lead 25 is connected through an inductance 36 to system ground, and that pacer lead 26 is connected through an inductance 37 to the input of sense amplifier 30. Diode 35 is connected between the leads as previously described, and individual feed-through capacitors 38 provide RF bypassing for each lead.

The amplified signal from amplifier 30, which contains little or no power line interference as a result of the notch filtering capability of sense amplifier 30, is applied to the R-wave detector 31. This detector compares the amplified sense signal with a predetermined reference level. When the sense signal exceeds this level, detector 31 produces an R-wave-indicative output signal which is applied to pulse control logic circuit 32 wherein it determined in the demand mode whether a pacer output pulse is required. In the event that an output pulse is required, logic control circuit 32 produces a control pulse which is applied to output circuit 33. This circuit responds to the control pulse to develop a heart stimulating pulse which is applied to pacer leads 25 and 26 through output capacitor 34.

To produce the output pulse, output circuit 33 requires a current supply having a voltage level greater than that of the pacer battery, which may typically have a nominal voltage level of 4.2 volts. Accordingly, pacer 10 includes a voltage multiplier circuit 40 which increases the voltage level of the unidirectional current from the pacer battery to a sufficient level for utilization by output circuit 33. This voltage multiplier circuit may be conventional in construction and operation.

The amplitude of the pulse produced by output circuit 33 is controlled by an output select circuit 41, which is in turn controlled by the previously described push button switches 15a and 15b. Depending on the pulse current level selected by circuit 41, 1 millisecond duration output pulses of either 2, 5, 10, 15 or 20 milliamperes are produced by the pacer. The selected output level is displayed by LCD 20 (FIG. 1), which together with LCDs 14, 16, 18 and 23 comprises part of display circuits 42 of the pacer.

The operating mode of cardiac pacer 10 is controlled by push button switches 19a and 19b (FIG. 1), which connect to pulse control logic circuit 32. Upon momentary actuation of these switches, logic circuit 32 is conditioned to the corresponding operating mode, and LCD 20 is conditioned to indicate the selected mode. The rate at which output heart stimulation pulses are produced is controlled by switches 13a and 13b (FIG. 1), which condition logic circuit 32 to operate at the selected rate, and LCD 14 to produce a corresponding rate display.

The sensitivity of cardiac pacer 10 to applied R-wave signals is determined by push button switches 17a and 17b (FIG. 1), which condition R-wave detector 31 to a selected sensitivity level. At the same time, a signal is applied to LCD 18 to provide an appropriate indication to the operator.

In accordance with conventional practice, the output of voltage multiplier 40 is applied to one terminal of the output capacitor 34 by means of a conventional filter network comprising a pair of series-connected resistors 43, 44 and a pair of capacitors 45 and 46 connected between the resistors and ground. A zener diode 47 limits the output voltage to a predetermined maximum level. The other terminal of output capacitor 34 is connected to the negative polarity input/output terminal 26 of the pacer through inductance 37. With this arrangement, output capacitor 34 is slowly charged by voltage multiplier 40 through resistors 43 and 44 and the load resistance presented by the heart until the capacitor becomes fully charged and assumes substantially the output voltage of the voltage multiplier circuit. The rate of charge is sufficiently low so as to not stimulate the associated heart muscles.

To provide a pacing pulse, output capacitor 34 is connected to ground by a high impedance discharge circuit comprising an NPN transistor 50 and a current control resistor 51. The impedance provided by this shunt circuit, and hence the discharge rate of output capacitor 34, is dependent on the conduction level of transistor 50.

During the charging of capacitor 34 in periods between output pulses transistor 50 is maintained non-conductive by a control signal applied to its base electrode through a transistor 52 and a resistor 53. In the absence of this control signal, the base electrode is maintained at a predetermined reference level by means of a diode 54 and a regulated unidirectional current source +REG of conventional construction. A resistor 55 is connected between the base electrode and ground.

In operation, control signals developed by pulse control circuit 32 periodically condition transistors 52 and 50 into conduction, allowing the previously charged output capacitor 34 to discharge through resistor 51 and the heart. During discharge the level of current flow and hence the energy level of the pacer pulse, is determined by the voltage at the emitter-base junction of transistor 50, which is in turn dependent on the opposing voltage developed at its emitter electrode, the base electrode voltage being held constant by diode 54. Thus, the lower the emitter circuit resistance, as comprised by resistor 51 and any resistances connected in shunt therewith, the heavier the emitter current in transistor 50 and the greater the pacer output pulse.

Once output capacitor 34 has discharged, the charging cycle begins anew and the capacitor is recharged by voltage multiplier 40 through resistors 43 and 44.

To provide the user with the capability of varying the current level of pacer output pulses, emitter resistor 51 is selectively shunt-circuited with selected ones of resistors 60, 61 and 62 individually connected to ground through the principal electrodes of respective ones of transistors 63, 64 and 65, and with selected ones of resistors 75, 76 and 77 individually connected to ground through the principal electrodes of respective ones of transistors 78, 79 and 80, and connected to resistor 51 through the principal electrodes of a field effect transistor (FET) 73. Transistors 63–65 and 78–80 are selectively conditioned into conductive states by means of control signals developed by output select circuit 41 and applied to the base electrodes of the transistors by respective ones of resistors 66–68 and 81–83. Depending on the control signals produced by output select circuit 41, none, 1, 2 or 3 of transistor pairs 63, and 78, 64 and 79, and 65 and 80, may be biased into conduction to decrease the effective emitter circuit impedance of transistor 50, thereby increasing the discharge rate of output capacitor 34.

In operation, the user selects an appropriate output current level by means of push button switches 15a and 15b, which condition output select circuit 41 to produce appropriate output control signals on output lines 70, 71 and 72. The particular output level selected is indicated by LCD 16, which comprises part of the system display module 42. In the illustrated embodiment output levels of 2, 5, 10, 15 and 20 milliamperes are possible. For a 2.0 milliampere output pulse the three outputs of output select circuit 41 are logic low, transistors 63–65 and 78–80 are non-conductive, and only resistors 51 and 74 are included in the emitter circuit of transistor 50 to determine the discharge current level. For a 5.0 milliampere output pulse a logic high signal is present on control line 72 and transistors 65 and 80 are rendered conductive, causing resistors 62 and 77 to be shunt-connected with resistors 51 and 74. The emitter impedance of transistor 50 now comprises the parallel combination of resistors 51, 74, 62 and 77, decreasing the emitter circuit impedance to provide the desired 5.0 milliampere pulse current level.

For 10 milliampere operation control lines 71 and 72 are conditioned logic high by output select circuit 41, causing transistors 64, 65, 79 and 80 to conduct and the emitter impedance of transistor 50 to comprise the parallel combination of resistors 51, 74, 61, 62, 76 and 77. For 15 milliampere operation control lines 70 and 72 are conditioned logic high, causing transistors 63, 65, 78 and 80 to conduct. The emitter circuit impedance of transistor 50 then comprises the parallel combination of resistors 51 and 74 and resistors 60, 62, 75 and 77 and the desired 15 milliampere discharge current rate is achieved. For 20.0 milliampere operation, all three control lines 70–72 are conditioned logic high, transistors 63–65 and 78–80 are conductive, and the current-determining emitter resistance comprises the parallel combination of resistors 51, 74, 60–62 and 75–77.

Thus, output select circuit 41 conditions appropriate ones of control lines 70–72 to provide a selected one of five discrete pulse current levels. In particular, the output circuit selects operating levels of either 2.0, 5.0, 10.0, 15.0 or 20.0 milliamperes. The determination is made by the physician by momentarily actuating either the up selector switch 15a, or the down selector switch 15b, with concurrent actuation of ENABLE switch 22.

In accordance with the invention, the output pulse level of cardiac pacer 10 may be instantaneously reduced to a predetermined fraction of its user-selected normal operating level by momentary actuation of the front panel mounted selector switch 15b. This switch reduces the output to one-tenth of its pre-selected level irrespective of whether ENABLE switch 22 is also engaged. As shown in FIG. 3, switch contacts 15b are connected to the gate electrode of N-channel enhancement-type field effect transistor (FET) 73.

The gate electrode of FET 73 is connected to ground by a bypass capacitor 84, by the normally-open contacts of switch 15b, and to a source of unidirectional voltage by a resistor 86. In normal operation, FET 73 is biased into conduction by current through gate pull-up resistor 86, causing resistor 74 and selected ones of resistances 75-77, as determined by the status of control lines 70-72, to be connected in shunt with resistor 51 to establish the normal operating level of the pacer.

In accordance with the invention, when determining the stimulation threshold, push button switch 15b is depressed, causing the control electrode of FET 73 to be grounded. This conditions FET 73 to cut-off, removing resistor 74 and the selected (for the selected operating current) ones of resistors 75-77 from parallel connection with resistor 51 and the selected ones of resistors 60-62. Thus, pacer output current is determined only by resistor 51 and the selected ones of resistors 60-62, and is consequently lower because of the higher resistance in the emitter circuit of transistor 50. By proportioning resistor pairs 74 and 51, 60 and 75, 61 and 76 and 62 and 77 the current reduction upon actuation of switch 15b can be made to equal a predetermined fraction of the selected operating level. In the illustrated embodiment this reduction is, for example, selected to be 1/10 of the normal operating level. This reduction level is particularly advantageous since it enables the threshold level to be directly read on existing indicators as 1/10 of the indicated level, and it provides a desirable capture threshold range of 0.2-2.0 milliamperes for normal operating levels of 2.0-20.0 amilliamperes.

In practice, for 2.0 milliampere operation control lines 70-72 are all logic low and transistors 63-65 and 80-82 are all non-conductive. With switch 15b open, as during normal operation, FET 73 is biased into conduction and the current level upon discharge of capacitor 34 is determined by the parallel combination of resistors 74 and 51. Should it be necessary to momentarily reduce this current level, as when determining the threshold level of the cardiac interface, the operator depresses switch 15b grounding the control electrode of FET 74 and causing that device to become non-conductive. As a result, only resistor 51 is in the emitter circuit of transistor 50, and the discharge takes place at a lower 1/10 current level.

At higher current levels the principle is the same. For example, when operating at 5.0 milliamperes, control line 72 is conditioned logic high by output select circuit 41 and transistors 65 and 80 are conditioned to conduct. This causes resistors 62 and 77 to be shunt-connected across resistors 51 and 74. When FET 73 is rendered non-conductive, as when switch contacts 15b are actuated, resistors 74 and 77 are disconnected to reduce the output current to 1/10 of its previously selected level.

Thus, the output of the cardiac pacer may be reduced at any time by actuation of a single push button to 1/10 of its operating level for the purpose of measuring the capture threshold level of the heart with which the pacer is being used. This can be done quickly without disturbing the operating setting of the pacer. Recapture of the heart can be obtained at any time by merely releasing the push button to return the pacer to its normal operating level. By selecting discrete operating levels within the range of 2.0 milliamperes to 20.0 milliamperes, and then depressing the push button switch discrete threshold levels of from 0.2 milliamperes to 2.0 milliamperes can be quickly evaluated.

It will be appreciated that various alternative control circuits are possible for controlling the conduction of transistor 73. For example, it would be possible to incorporate logic circuitry in select circuit 41 to provide an appropriate control signal upon actuation of switch 15b.

While a particular embodiment of the invention has been shown and described, it will be obvious to those skilled in the art that changes and modifications may be made without departing from the invention in its broader aspects, and, therefore, the aim in the appended claims is to cover all such changes and modifications as fall within the true spirit and scope of the invention.

We claim:

1. A cardiac pacer for use in conjunction with an external pacer lead for developing recurrent pacing pulses of predetermined current amplitude, comprising:
   an output terminal for establishing electrical communication with the pacing lead;
   a plane of reference potential;
   a unidirectional current source for developing relative to said plane of reference potential a unidirectional pacing current;
   a pacing output capacitor, one terminal of said capacitor being connected to said unidirectional current source and the other terminal of said capacitor being connected to said output terminal;
   pacer control circuit means for producing a pacing control signal for controlling the occurrence of pacing pulses;
   switch means responsive to said pacing control signal connected between said one terminal of said capacitor and said plane of reference potential for connecting said capacitor to said output terminal upon the occurrence of each control pulse whereby said capacitor discharges through the pacing lead to produce a pacing pulse;
   current limiting means comprising an output resistor in series circuit relationship with said switch means and said capacitor for controlling the discharge of said capacitor through the pacer lead;
   pulse amplitude control circuit means responsive to a user-initiated input for producing a pulse amplitude control signal;
   a predetermined plurality of primary shunt resistors;
   first switching circuit means responsive to said output control signal and including a plurality of switch devices individually associated with respective ones of said primary shunt resistors for connecting selected ones of said primary shunt resistors in parallel-circuit relationship to said output resistor to selectively provide one of a plurality of predetermined pacing pulse amplitudes during a first operating mode of the pacer;
   a plurality of secondary shunt resistors of like number to and in correspondence one for one with said predetermined plurality of primary shunt resistors;
   second switching circuit means responsive to said output control signal and including a plurality of switch devices individually associated with respective ones of said secondary shunt resistors for connecting in parallel-circuit relationship with said output resistor those of said plurality of secondary shunt resistors which correspond to those of said plurality of primary shunt resistors selected by said first output control circuit means; and
   user-actuable mode control means for connecting said selected secondary shunt resistors in parallel with said output resistors in a first mode of operation, and for interrupting said connections in a second mode of operation and said selected ones of said primary shunt resistors to selectively reduce the amplitude of the pacer pulse to a predetermined fraction of the pulse amplitude selected in said first mode of operation.

2. A cardiac pacer as defined in claim 1 wherein said mode control means comprise a mode-selection switch device serially connected between said output resistance and said parallel-connected secondary shunt resistors.

3. A cardiac pacer as defined in claim 2 wherein said the pacer includes a user-actuated mode switching circuit for supplying a mode control signal and said mode-selection switch device comprises a transistor having principal electrodes connected between said output resistance and said parallel-connected secondary shunt resistors, and a control electrode connected to said mode switching circuit for receiving said mode control signal.

4. A cardiac pacer as defined in claim 3 wherein said mode control circuit includes a user-actuable push button switch for selecting said second mode of operation.

5. A cardiac pacer as defined in claim 1 wherein the resistances of said primary shunt resistors and said secondary shunt resistors are proportioned to provide a constant predetermined ratio between the amplitude selected in said first mode and the amplitude provided in said second mode of operation.

6. A cardiac pacer as defined in claim 5 wherein said constant predetermined ratio is 10:1.

* * * * *